United States Patent [19]

Wilmore

[11] Patent Number: 5,276,018
[45] Date of Patent: Jan. 4, 1994

[54] COMPOSITION COMPRISING AMINO ACIDS AND METHODS FOR DECREASING MUSCLE BREAKDOWN

[75] Inventor: Douglas W. Wilmore, Brookline, Mass.

[73] Assignee: Brigham and Women's Hospital, Boston, Mass.

[21] Appl. No.: 914,566

[22] Filed: Jul. 17, 1992

[51] Int. Cl.$^5$ .................... A61K 31/40; A61K 31/195
[52] U.S. Cl. ........................ 514/23; 424/439; 424/DIG. 13; 426/804; 426/810; 514/400; 514/893; 514/921
[58] Field of Search ........... 514/23, 893, 921, 400; 424/439, DIG.; 426/804, 810

[56] References Cited

U.S. PATENT DOCUMENTS

| | | | |
|---|---|---|---|
| 4,296,127 | 10/1981 | Walser | 514/893 |
| 4,675,196 | 6/1987 | Villa et al. | 514/893 |
| 4,677,121 | 6/1987 | Walser et al. | 514/893 |
| 4,678,807 | 7/1987 | Cotter et al. | 514/893 |
| 4,690,820 | 9/1987 | Simko | 514/893 |
| 4,703,062 | 10/1987 | Blackburn et al. | 514/893 |
| 4,767,785 | 8/1988 | Geogieff | 514/561 |
| 4,780,475 | 10/1988 | Cerra et al. | 514/561 |
| 4,818,516 | 4/1989 | Metcoff | 514/561 |
| 5,039,704 | 8/1991 | Smith et al. | 514/563 |
| 5,102,910 | 4/1992 | Mittheiss et al. | 514/893 |

*Primary Examiner*—Ronald W. Griffin
*Attorney, Agent, or Firm*—Sterne, Kessler, Goldstein & Fox

[57] ABSTRACT

The present invention provides compositions and methods for decreasing tissue breakdown in mammals. Specifically, tissue breakdown in a mammal can be decreased by the administration of composition, wherein said composition comprises from about 35% to 50% essential amino acids of which from about 18% to 30% are branched chain amino acids, and from about 50% to 65% non-essential amino acids, wherein the non-essential amino acids comprise from about 5% to 15% ALA and from about 15% to 45% GLN. In addition, the present invention provides methods of preparing compositions which are capable of meeting the specific metabolic needs of a patient experiencing catabolic tissue breakdown.

10 Claims, No Drawings

COMPOSITION COMPRISING AMINO ACIDS AND METHODS FOR DECREASING MUSCLE BREAKDOWN

BACKGROUND OF THE INVENTION

1. Field of the Invention

The present invention relates to the field of nutritional therapy. Specifically, the present invention provides novel compositions containing the necessary amino acids which, when administered to a mammal, are capable of decreasing the catabolic breakdown of body tissue. Such breakdown can be associated with acute catabolic states or injury, medical therapies such as the use of anti-inflammatory agents, and acute exercise.

2. Description of the Background Art

The breakdown of body tissue can be associated with a variety of catabolic conditions as well as a side effect of various medical treatments. Catabolic breakdown of body tissue occurs in patients during semistarvation (Pozefsky et al., *J. Clin. Invest.* 57:444-449 (1976)), prolonged fasting (Felig et al., *J. Clin. Invest.* 48:584-594 (1969)), acute exercise (Felig et al., *J. Clin. Invest.* 50:2703-2714 (1971)), injury (Aulick et al., *Surgery* 85:560-565 (1982)), protein feeding (Abumrad et al., *Metabolism* 31:463-470 (1982)), infection (Fong et al., *J. Clin Invest.* 85:1896-1904 (1990)), trauma (Brooks et al., *J. Surg. Res.* 40:395-405 (1986)), and steroidal therapy especially glucocorticoids (Kaplan S. A. and Shimizu, C. S.; *Endocrinology* 72:267-272 (1963); Ryan W. and Carver, M., *Proc. Exp. Biol. Med.* 114:816-819 (1963); Muhlbacher F. et al., *Am. J. Physiol.* 247:E75-E83 (1984)).

As a result of each of the above, patients experience a marked decrease in tissue mass due to catabolic breakdown. The mechanism leading to the tissue breakdown is unclear; however, it has been postulated that tissue breakdown is but one of the bodily defenses which is mounted against injury, the effect being to increase the inter- and intracellular supply of amino acids. Such amino acids supply the necessary elements for other metabolic activity (such as replication and function of immune and other cells and wound repair) as well as supplying energy.

In general, patients suffering from a severe acute catabolic state can require some type of nutritional therapy. The nutritional requirements of these patients are met through the administration of either an enteral or parenteral diet. Enteral diets are usually administered using small-bore tubing which is placed through the nose into the gastric, or duodenal regions, or through surgical implantation as in, for example, gastrostomy, or jejunostomy.

Parenteral diets are usually administered intravenously (i.v.). These i.v. fluids are sterile solutions composed of simple chemicals such as, for example, sugars, amino acids, and electrolytes, which can be easily assimilated.

The term "total parenteral nutrition" (TPN) is used to describe formulas for use in patients who derive their dietary requirements intravenously. Total parenteral formulas, unlike enteral formulas, do not normally contain the non-essential amino acid glutamine (GLN). The absence of GLN from parenteral formulas is due, in part, to the long standing belief that GLN belongs to those non-essential amino acids which do not need to be administered in appreciable amounts to patients undergoing TPN. Additionally there is concern with breakdown of GLN because of long-term instability at room temperature and especially during heat sterilization which results in generation of ammonia and pyroglutamic acid. A lesser concern has been the generation of glutamic acid from GLN because of the potential toxicity of glutamic acid as a neurotransmitter. This is not a clinically important problem, for glutamic acid is found in many commercially available intravenous amino acid formulas.

Glutamine has been included in several enteral formulations. These include Vivonex, Immun-Aid or Alitraq (see Table 5). In general, these formulations have been generated by adding free glutamine to a high biological protein source. No parenteral nutrient solutions containing glutamine are commercially available; experimental solutions have been constructed by adding dipeptides of L-glutamine to standard formulas (Stehle et al., *Lancet* 1:231-233 (1989), Hammarqvist et al., *Ann. Surg.* 209:455-461 (1989)). However, as discussed later, these formulations have not been designed to reflect the various amino acids released during catabolism.

Until now, enteral and parenteral diets have been formulated to provide the energy and amino acids necessary to achieve positive nitrogen balance in normal individuals. However, the various formulations available are generally based on the dietary requirements of a normal individual and increase or only slightly after these requirements for the commonly seen acute catabolic states. As such, current nutritional therapy does not eliminate tissue catabolism (Warnold et al., *Ann. Surg.* 208:143-149 (1988); Iapichino et al., *Crit. Care Med.* 18:1367-1373 (1990)).

DESCRIPTION OF THE PREFERRED EMBODIMENTS

The present invention is based on three observations. First, that catabolic tissue breakdown increases the release into the bloodstream of a highly specific group of amino acids, especially GLN and alanine (ALA). Table 1 provides a summary of the various amino acids released from the skeletal muscle of patients with a variety of acute catabolic conditions.

TABLE 1

The afflux of amino acid nitrogen from an extremity (representing primary skeletal muscle) during a catabolic illness[+]
% of Total, Mean (Range)

| | |
|---|---|
| Essential amino acids | 23 (19-28) |
| Branched chain amino acids | 9 (7-12) |
| Non-essential amino acids | 76 (75-80) |
| Glutamine | 26 (8-34) |
| Alamine | 23 (14-32) |

[+]Fong Y. et al. J. Clin. Invest. 85:1896-1904 (1990)
Loder P. B. et al. Ann. Surg. 211:360-368 (1990)
Brooks D. et al. J. Surg. Res. 40:395-405 (1986)

Second, glucose can act to inhibit some levels of catabolic tissue breakdown. (Brooks et al., *J. Surg. Res.* 40:395-405 (1986); Iapichino et al., *Crit. Care Med.* 18(12):1367-1373 (1990)). Table 2 provides a summary of the most extreme effects of glucose on the amino acid released from skeletal muscle in patients with catabolic conditions and trauma generated during fixed hyperglycemia. When glucose is supplied to a patient, the release of alanine from skeletal muscle decreases.

TABLE 2

The efflux of amino acids from skeletal muscle in catabolic states during basal state and glucose infusion.
(− = release, + = uptake, nM/100 ml/min, mean ± SEM)

|  | Basal | Steady state glucose infusion |
|---|---|---|
| Glutamine | −116 ± 92 | −192 ± 96 |
| Glutamate | −53 ± 29 | −4 ± 21 |
| Alanine | −414 ± 141+ | −41 ± 61* |
| Taurine | −99 ± 78 | 57 ± 34 |
| Aspartic Acid | −74 ± 30+ | 29 ± 19* |
| Threonine | −243 ± 65+ | −66 ± 12 |
| Serine | −122 ± 65 | −22 ± 18 |
| Asparagine | −256 ± 140+ | −7 ± 21 |
| Proline | −103 ± 145 | 5 ± 62 |
| Glycine | −328 ± 40+ | 2 ± 40 |
| Cystine | −66 ± 30+ | 10 ± 59 |
| Valine | −231 ± 42+ | 7 ± 59* |
| Isoleucine | −105 ± 39+ | 10 ± 15* |
| Leucine | −153 ± 57 | 6 ± 16* |
| Tyrosine | −49 ± 16+ | −27 ± 17 |
| Phenylalanine | −42 ± 28 | −19 ± 2 |
| Ornithine | −60 ± 5+ | −6 ± 48 |
| Lysine | −253 ± 64+ | −55 ± 28 |
| Histidine | −53 ± 17+ | −15 ± 11* |
| Arginine | −61 ± 20+ | −7 ± 30 |
| Phosphoserine | −48 ± 17 | −34 ± 13 |
| Total branched chain amino acids | −460 ± 134* | 10 ± 82* |
| Total nitrogen flux | −3843 ± 1383+ | −819 ± 314* |

+Different from normal control values $p < 0.05$
*Different from basal $p < 0.05$
From: Brooks D. et al., J. Surg. Res. 40:395–405 (1986)

Third, formulations which are intended to provide the required amount of amino acids for the catabolic patient need to contain almost twice the calculated requirements of the normal mammal. This reflects the increased turnover rate of amino acids during catabolism and the inefficiency of our present formulations.

Utilizing these observations, the present invention provides formulations which, when administered to a mammal, are capable of decreasing the catabolic breakdown of muscle tissue and diminishes net loss of body protein.

Specifically, the compositions of the present invention differ from current dietary supplements in that they contain from about 50–65% non-essential amino acids including both alanine and glutamine and that essential amino acid concentration has been decreased to 35% to 50%. In detail, the preferred composition of the present invention contains from about 35% to 50% essential amino acids, of which 18–30% is branch chain amino acids (BCAA), and from about 50% to 65% non-essential amino acid, of which 15–45% is glutamine, and 10–25% is alanine. The most preferred composition contain 20–35% glutamine.

In another embodiment of the present invention, 10–25% glucose is added to the composition. By supplementing the compositions of the present invention with glucose, the amount of ALA present can be reduced to 5–15%.

As used herein, the term "mammal" is intended to include, but not be limited to, humans, horses, pigs, cattle, cats, dogs and rodents.

As used herein, "body tissue" or "tissue" is intended to include all body parts whose mass decreased during catabolic breakdown. This includes, but is not limited to, muscle tissue, intestinal tissue such as the bowel, pancreatic tissue, hepatic tissue, immunological tissue such as lymph nodes, spleen and fixed macrophages, and hematologic tissues.

As used herein, essential amino acids are those not synthesized by mammals. These include leucine, isoleucine, valine, methionine, lysine, threonine, phenylalanine, tryptophan and histidine. Table 3 provides the preferred amounts of the various essential amino acids which are included in the compositions of the present invention.

TABLE 3

| Ideal Composition, Essential Amino Acids | |
|---|---|
| | g % or g/100 g |
| Leucine | 5–10 |
| Isoleucine | 4–10 |
| Valine | 5–10 |
| Methionine | 4–6 |
| Lysine | 3–5 |
| Threonine | 3–5 |
| Phenylalanine | 3–5 |
| Tryptophan | 1–2 |
| Histidine | 3–5 |

As used herein, non-essential amino acids are those synthesized by mammals. These include but are not limited to arginine, proline, alanine, glycine, serine, tyrosine, aspartate, glutamate and glutamine. Table 4 provides the preferred amounts of the various non-essential amino acid which are included in the compositions of the present invention.

TABLE 4

| Ideal Composition, Non-essential Amino Acids | |
|---|---|
| | g % or g/100 g |
| Arginine | 5–12 |
| Proline | 3–5 |
| Alanine | 5–15 |
| Glycine | 2–10 |
| Serine | 2–7 |
| Tyrosine | 0–2 |
| Aspartate | 0–5 |
| Glutamate | 0–6 |
| Glutamine | 15–45 |

Table 5 provides a comparison of the composition of the present invention and other enteral diets which contain amino acids including supplemental glutamine. As can be seen in the table, the concentration of various amino acids as determined by muscle breakdown profiles differs from previous compositions which are based solely on available hydrolyzed protein base solutions with or without amino acid supplementation. For example, Vivonex and Immun-Aid do not contain adequate amounts of glutamine, relative to other amino acid constituents. Vivonex contains an excessive quantity of leucine. Immun-Aid has too little methionine, histidine, proline and alanine compared to the formulation based on muscle proteolysis. Finally, while Alitraq has sufficient glutamine, it lacks adequate alanine, is low in proline and has excessive phenylalanine and lysine. No commercially available or experimentally used solutions (save the example used in this description) have any similarities to the composition described.

TABLE 5

Comparison of suggested formulation with enteral products containing sufficient glutamine. g/100 g

| | Suggested Formulation | Vivonex Ten | Immun-Aid+ | Alitraq |
|---|---|---|---|---|
| leucine | 5-10 | 16.6*** | 14.5*** | 8.2 |
| isoleucine | 5-10 | 8.3 | 9.6 | 4.9 |
| valine | 5-10 | 8.3 | 11.85 | 5.8 |
| methionine | 4-6 | 3.7 | 1.0 | 4.1** |

TABLE 5-continued

Comparison of suggested formulation with enteral products containing sufficient glutamine, g/100 g

| | Suggested Formulation | Vivonex Ten | Immun-Aid+ | Alitraq |
|---|---|---|---|---|
| lysine | 3-5 | 5.1 | 3.7 | 6.5 ↑ |
| threonine | 3-5 | 4.0 | 2.6 ↓ | 4.6 |
| phenylalanine | 3-5 | 5.2 | 1.9 | 6.4* ↑ |
| tryptophan | 1-2 | 1.3 | 1.3 | 1.35 |
| histidine | 3-5 | 2.4 | <u>1.3</u> | 2.0 |
| arginine | 5-12 | 7.6 | 17.8*** | 8.5 |
| proline | 3-5 | 4.9 | <u>0.6</u> | 2.0 ↓ |
| alanine | 5-15 | 5.2 | <u>1.6</u> | <u>3.0</u> |
| glycine | 2-10 | 4.0 | 2.3 | 2.0 |
| serine | 2-7 | 2.9 | 2.9 | 2.0 |
| tyrosine | 1-2 | 0.8 | 1.3 | 2.1* |
| aspartate | 0-5 | 7.0 ↑ | 0 | 4.4 |
| glutamate | 0-6 | 0 | 2.3 | 5.1 |
| glutamine | 15-45 | <u>12.8</u> | <u>13.6</u> | 28.9 |
| asparagine | 0-2 | 0 | 4.2 | 0 |
| cystine | 0-3 | | 2.6 | 0.4 |
| other | | | | |

\* = based on lactalbumin sequence and known supplemental amino acids
<u></u> = inadequate amount
↑ ↓ = increase or decrease outside of ideal range
*total 8.5 g as PHE/TYR - distributed as 75:25
**total 4.5 g of methionine/cystine, quantity based on original composition
***supplemented for a specific purpose A mammal is said to be suffering from catabolic tissue breakdown when the mammal experiences a decrease in tissue mass as a result of catabolic activity. A variety of tests can be employed to determine if a mammal is suffering from tissue breakdown. These include, but are not limited to, collection of urine and analysis for urea, total nitrogen and 3-methylhistidine (Grant A. and De-Hoog S., *Nutritional Assessment and Support*, 1991, pp 112-114, p 401, Seattle, Wash.).

As used herein, a composition is said to "decrease tissue breakdown" when a decrease in the level of tissue breakdown and/or the loss of protein from the body is observed following the administration of the compositions of the present invention.

The methods of the present invention for decreasing tissue breakdown in a mammal are suitable for the treatment of a large number of catabolic states and pathological conditions. Since the methods of the present invention are directed to the actual tissue breakdown and are not directly a treatment for the condition causing the muscle catabolism per say, the methods of the present invention can be utilized to treat a majority of the conditions which result in tissue breakdown. These include, but are not limited to, trauma, infection, burn injury and prolonged physical activity.

An illustration of this is the use of the methods of the present invention to reduce muscle breakdown in a mammal which is being treated with an anti-inflammatory agent. Anti-inflammatory agents, especially glucocorticoids such as prednisone, stimulate tissue breakdown. Therefore, the compositions of the present invention, when administered accordingly, are effective in ameliorating one of the negative side effects of such drug therapies.

The composition of the present invention can be prepared by a variety of means known in the art including hydrolysis of known proteins or synthesis of the individual amino acids. In general, the compositions are prepared by mixing the appropriate amounts of amino acids together in a form suitable for administration using standard formulation procedures and guidelines.

The compositions of the present invention may be administered by any means or route, as long as they achieve their intended purpose. Amounts and regimes for the administration of the amino acid compositions of the present invention can be readily determined by those with ordinary skill in the art. For example, administration of the agents of the present invention may be by parenteral, or enteral routes. Preferably the compositions of the present invention are provided from the dose of 1 to 1.5 g of the amino acid mixture/kg/day.

As used herein "parenteral" is defined as that region outside the digestive tract. Examples of parenteral administration include, but are not limited to, routes such as subcutaneous, intramuscular, or intravenous injection, nasopharyngeal or mucosal absorption, or transdermal absorption.

Preparations for parenteral administration includes sterile aqueous or non-aqueous solutions, suspensions and emulsions. Carriers can be included in the formulation to increase or enhance absorption.

As used herein, "enteral" is defined as that portion of the alimentary canal including the stomach and the portion distal to the stomach. Enteral administration can be accomplished by tubing placed via the nose into the gastric or duodenal regions.

Preparation for enteral administration include sterile aqueous solutions, suspensions and emulsions as well as non-aqueous formulations. Carriers can be included in the formulation to increase or enhance absorption.

The amount of the composition administered to the mammal will vary depending upon the needs of the mammal. For a mammal with increased metabolic demands, it is preferable to administer the composition at frequent intervals throughout the day. Depending upon the severity of the syndrome, the composition can be administered intravenously, or can be incorporated into the diet provided to the mammal in a tube feeding with exact chemical composition,' in a drink or as flavored wafers, pills or powder.

The compositions of the present invention can be administered either alone or as a dietary supplement. When used as a dietary supplement, the composition can be mixed with an existing enteral or parenteral diet prior to administration to the patient. For example, the various amino acids can be used to supplement the standard total parenteral nutrition (TPN) formulation. Alternatively, the compositions of the present intervention can be administered separately without mixing it directly with other components of the diet.

A further embodiment of the present invention is based on the observation that the nutritional requirements, specifically the need for non-essential amino acids, depends on the physiological makeup of the individual (based on sex and age of the individual and physical condition which determines the size of the muscle mass) as well as the specific condition such as immunological status and degree of acidosis.

Based on this observation, the present invention provides methods of preparing compositions which are capable of meeting the specific metabolic needs of a patient experiencing catabolic tissue breakdown. Such compositions are capable of decreasing the rate of tissue catabolism.

In detail, the components of such compositions are determined by identifying the types and amounts of amino acids which are released in the patient due to catabolic muscle breakdown with specific emphasis on the non-essential amino acid component.

Any one of a variety of procedures may be employed to determine a profile of the types and concentration of amino acids released in a patient. These include, but are not limited to, the measurement of efflux of amino acids from skeletal muscle (Aoki T. T. et al., *Am. J. Clin. Nutr.* 29:340-350 (1976); Finley R. J. et al., *Surg Forum* 30:76-77 (1979); Aoki T. T. et al., *J. Clin. Invest.* 68:1522-1528 (1981)).

Once the amino acid profile is determined, one skilled in the art can readily prepare a composition by adding from about 1 to 2 times the concentration of each of the specific amino acids released in the patient to a standard enteral or parenteral diet utilizing procedures known in the art or those described earlier.

Since the specific needs of an individual patient may vary during the course of the catabolic condition, an amino acid profile can be determined on a regular schedule and the composition varied accordingly.

Having now generally described the invention, the methods and agents will be more readily understood through reference to the following examples. These examples are provided by way of illustration and are not intended to limit the present invention unless specified otherwise.

EXAMPLE 1

To test this new solution, we performed a randomized, prospective, double-blind study comparing a standard intravenous amino acid formula with the new mixture formulated by the guidelines previously described in patients undergoing allogeneic bone marrow transplantation. The study patients were 18-60 years of age and had acute myelogenous leukemia (AML) in first remission, myelodysplasia, or chronic myelogenous leukemia (CML) in stable or accelerated phase. Twenty-one patients had major histocompatibility complex (MHC) compatible donors, and three patients had sibling or parental donors that were mismatched at a single MHC locus (Table 5). The patients were clinically stable, with normal neurological examinations, hepatic function, renal function and glucose tolerance. They were not below 90% of ideal body weight prior to entry, but were considered to require intravenous nutritional support following transplantation. The study was approved by the Committee for the Protection of Research Risks, Brigham and Women's Hospital. Written informed consent was obtained from each participant. The procedure describing the patient's care, chemotherapy and bone marrow transplantation have been previously described (Ziegler T. et al., *Ann. Int. Med.* 116:821-828 (1992)). A member of the study team initially assessed all patients for measurement of height, weight, mid-arm circumference, skinfold thickness, serum albumin and oral dietary intake. Calorie requirements were based on previous studies that determine requirements for energy balance in this population. Basal energy requirements based on sex, age, height and weight were determined from standard tables and this factor was multiplied by 1.5 to estimate energy requirements for bone marrow transplant patients. Patients received 1.5 g protein/kg/day. The quantity of calories provided by protein was subtracted from energy requirements to calculate nonprotein calories, 70% of which were given as glucose and 30% as lipid emulsion (Intralipid, Kabi Vitrum, Stockholm, Sweden). Adequate vitamins, minerals, and trace elements were also added daily. Electrolytes were varied daily to maintain normal serum concentrations of these substances. In subjects >12% above ideal body weight, these calculations were based on the upper limit of ideal body weight as determined from the midpoint obtained from standard tables.

Patients were then randomized to receive either a commercially available amino acid solution or the solution containing 3.9 mmol glutamine/kg. Patients entered into the study were randomized by the research pharmacists who balanced the study groups for diagnosis, treatment and gender. All other individuals participating in the study, the primary care providers, and the patients were blinded as to which of the two nutrient solutions was administered. After 24 patients were studied utilizing the two diets, the code was broken and the data analyzed.

The control solution was a standard balanced crystalline amino acid formula (Novamine, Kabi Vitrum, Stockholm, Sweden) which did not contain glutamine. The solution containing glutamine was mixed in the hospital manufacturing pharmacy by combining a commercially available amino acid solution (Renamine, Baxter Health Care Corp., McGaw Park, Ill.) containing a high proportion of essential amino acids with the crystalline non-essential amino acid L-glutamine (Ajinomoto USA, Inc., Raleigh, N.C.). This solution was designed to provide 18.7 mmol glutamine/100 ml solution (2.73 g/100 ml, Table 6). After appropriate mixing, the solution was sterilized by membrane filtration (Hepafil, Millipore, Bradford, Mass.) and stored at 4° C. for up to eight days.

TABLE 6

| COMPOSITION OF AMINO ACID FORMULAS | | |
|---|---|---|
| Amino Acid (mg/100 ml) | Standard Formula+ | Glutamine-Supplemented Formula* |
| Leucine | 790 | 324 |
| Isoleucine | 570 | 270 |
| Valine | 730 | 443 |
| Methionine | 570 | 270 |
| Lysine | 900 | 243 |
| Threonine | 570 | 205 |
| Phenylalanine | 790 | 265 |
| Tryptophan | 190 | 86 |
| Histidine | 680 | 227 |
| Arginine | 1120 | 340 |
| Proline | 680 | 189 |
| Alanine | 1650 | 302 |
| Glycine | 790 | 162 |
| Serine | 450 | 162 |
| Tyrosine | 30 | 22 |
| Aspartate | 330 | 0 |
| Glutamate | 570 | 0 |
| Glutamine | 0 | 2727 |
| Total mg/100 ml | 11410 | 6237 |
| % AA/100 ml | 11.4% | 6.24% |

+Novamine
*Renamine-base amino acid solution

Each morning a parenteral nutrition order was completed by adjusting the concentrations of electrolytes provided in the parenteral nutrition as indicated by the clinical condition of the patient and serum electrolytes. All other components of the solution (including the quantity of macronutrients and the specific amino acid solution utilized) were fixed throughout the study. The solution was compounded by the pharmacy using an automated computed mixing device (Auto-Mix, Baxter Health Care Corporation, McGaw Park, Ill.) and all components of the daily nutritional prescription were added to a three liter bag. Each day at 4 p.m. the nutrient bag was replaced with the new prescription and the new solution was infused at a constant rate over the next 24 hours.

Thus, isocaloric and isonitrogenous diets varying only in amino acid composition were administered to a relatively homogenous patient group. Although minor variations occurred in the quantity of essential amino acids administered in the two diets (45% in the control solution vs 33% in the glutamine-containing solution), the major alteration in the parenteral nutritional formula was the quantity of glutamine administered, which for a 70 kg person represented either zero or 274 mmol/day.

Criteria were established to facilitate alterations in the nutrient solution in response to potential complications including alteration in mental status, organ failure, metabolic abnormalities (i.e., hyperglycemia and hypertriglyceridemia), fluid overload and violations of the dedicated infusion line. These modifications are typically those followed during the administration of central venous parenteral nutrition and are outlined in a practice manual.

Each day the patients were evaluated by a member of the study team and the 24-hour intakes of both enteral and parenteral calories and protein were determined. In addition, the mean oral temperature (from at least 8 determinations/day) and maximal oral temperature for the previous 24-hour period were recorded along with all drugs and blood products administered.

Between days 4 and 11, after marrow transplant all urine, stool and vomitus were collected in 24-hour pools for determination of nitrogen loss in those patients receiving parenteral nutrition. Pure urine samples from 3 consecutive days during the latter part of the first balance period were analyzed for 3-methylhistidine and creatinine. Blood samples were obtained weekly and analyzed for amino acids, glutamine and glutamate, ammonia, C-reactive protein and prealbumin. Hand grip strength was assessed initially and at two-week intervals throughout the study using a dynamometer (Asimow Engineering Co., Los Angeles, Calif.). Triceps skinfold, mid-arm circumference, and calculated arm muscle area measurements were made initially and at hospital discharge. All body weight measurements were recorded.

At the time of manufacture, all infusion bags were weighed and the volume calculated from the specific gravity of the contents. At the end of each 24-hour infusion the remaining volume was measured and subtracted from the initial volume. Concentrations of nitrogen in the nutrient solution as specified on the manufacturer's label were multiplied by the volume to determine total nitrogen intake. These concentrations were similar to laboratory measurements which were performed weekly. Total infused volume of parenteral nutrition was used to determine the total amount of protein, glucose and fat emulsion administered. Additional calories derived from other intravenous dextrose-containing solutions and oral intake of calories and nitrogen were also calculated daily. All urine, stool and mixed urine and stool losses were collected in 24-hour pools which corresponded to the time period that each nutrient bag was infused. Nitrogen and creatinine concentrations were multiplied by daily volume of urine and stool to determine daily nitrogen losses.

In order to insure accuracy of the urine and stool collections, the volume of losses recorded on the clinical record was compared to the measured volume of each 24-hour collection. If there was a difference of more than 15% between these volumes, the daily amount of creatinine excreted was compared to other days when the recorded and measured 24-hour volumes were comparable. When the amount of creatinine excreted was more than 20% below values obtained from other days, the excretion volume was adjusted so that creatinine excretion was comparable to the average creatinine loss for days when collections were deemed satisfactory. This correction was necessary for approximately 20% of the study days, and these periods were evenly distributed throughout both treatment groups. Inclusion or exclusion of these days did not alter the interpretation of the nitrogen balance data. Nitrogen balance was determined by subtracting all measured nitrogen losses from total nitrogen intake.

White blood cell count, blood glucose and renal and hepatic function tests were measured frequently (usually daily) as required for clinical care and analyzed using standard clinical laboratory techniques. All collected fluid losses were analyzed for content of creatinine and total nitrogen using a chemiluminescent technique (Antek Instruments, Houston, Tex.). The nitrogen content in the bag of parenteral nutrients was determined at least once weekly by the Kjeldahl method. Plasma ammonia was determined by an enzymatic method. Plasma glutamine and glutamate concentrations were determined by high performance liquid chromatography. Concentrations of other amino acids were determined using the Beckman Amino Acid Analyzer 6300 (Beckman Instruments, Brea, Calif.). Serum concentrations of prealbumin and C-reactive protein were determined using rate nephelometry (Beckman Array Protein Analyzer, Brea, Calif.). Urinary measurements of 3-methylhistidine were determined using reverse phase high-pressure liquid chromatography (Waters 840 HPLC System, Milford, Mass.), and urinary lactulose and mannitol concentrations were measured by enzymatic methods.

Prior to initiation of the study, criteria for patient exclusion from the entire study or from the analysis of certain portions of the study were established. Of the many exclusion criteria listed, only three were necessary. First, patients taking more than 50% of their nutrient requirements by the oral route during the hospitalization were totally excluded from the study. Patient data was not included in the nitrogen balance analysis if glucocorticoids were administered or if the patient was judged hemodynamically unstable during the balance study.

Statistical analyses were performed using SAS software, version 6.03 for the personal computer (SAS Institute, Cary, N.C.). Paired and unpaired t-tests or the Mann-Whitney U test were used as appropriate for single comparisons. Results from controls and glutamine-treated subjects at different times were compared using repeated measures analysis of variance (ANOVA) to determine the effect of treatment on the responses observed. In analyzing the effect of glutamine-supplemented parenteral feeding, the influence of covariates such as weight, sex, mean daily and peak daily temperature, nitrogen intake, antibiotic use and C-reactive protein concentration were also assessed. Differences in outcome variables, such as hospital days, and antibiotic and transfusion requirements, were tested using Fisher's exact test after determining the median value and testing the distribution of occurrences above and below the value by chi-square techniques. Because patients were maintained on parenteral nutrition for a variable period of time, effects of parenteral nutrition on blood concentrations were determined for the first 21 days when all patients were receiving complete infusion of the parenteral nutrients. All laboratory data were analyzed by ANOVA to evaluate the contribution of treatment and the effect of time on the response. Probability values $\leq 0.05$ were considered statistically significant.

RESULTS

Twenty-five patients were initially enrolled in the study. One patient was excluded from the analysis because he consumed more than 50% of his nutrient requirements orally throughout his hospitalization. The remaining 24 patients were comparable in age, sex distribution, weight, neoplastic disease, nutritional status and treatment when they entered the study (Table 7). One patient who required corticosteroid therapy for allergic reactions following blood transfusions during the initial ten days of study was not included in the initial nitrogen balance analysis. Calorie and nitrogen administration was maintained at comparable levels in the two groups throughout the study (Table 8). More than 85% of the total energy and protein intake was provided by the intravenous route for each study group during the period of parenteral feeding.

TABLE 7
PATIENT CHARACTERISTICS AT STUDY ENTRY
(Mean ± S.E.M. or range)

|  | Standard | Glutamine-supplemented |
|---|---|---|
| N | 11 | 13 |
| Sex |  |  |
| F | 6 | 8 |
| M | 5 | 5 |
| Age (yr) | 32 | 33 |
|  | (20–48) | (20–49) |
| Weight (kg) | 69.4 | 68.7 |
|  | (57.0–83.3) | (54.5–92.5) |
| % Ideal Body Weight (%) | 110 ± 5 | 106 ± 2 |
| Body Surface Area ($m^2$) | 1.76 | 1.76 |
|  | (1.54–2.12) | (1.44–2.10) |
| Triceps Skinfold Thickness (mm) | 17.9 ± 3.2 | 16.7 ± 1.9 |
| Midarm muscle circum. (cm) | 24.2 ± 1.0 | 24.0 ± 1.5 |
| Percent of Standard | 65.6 ± 8.5 | 53.9 ± 10.3 |
| Arm Muscle Area ($cm^2$) | 50.8 ± 4.2 | 54.8 ± 5.9 |
| Percent of Standard | 77.9 ± 7.4 | 79.4 ± 5.7 |
| Serum Albumin (g/L) | 45 ± 1 | 46 ± 1 |
| Diagnosis AML | 3 | 5 |
| CML | 8 | 8 |
| Therapy ARA-C, cytoxan, TBI | 11 | 13 |
| GVHD prophylaxis ST-1 immunotoxin | 6 | 9 |
| Cyclosporin/Methotrexate | 5 | 4 |
| Unmatched Donors | 1 | 2 |

During the initial balance period (days 4–11 post transplant), both intravenous and oral calorie and nitrogen intakes were comparable between the two groups and provided approximately 118% of the energy and 100% of the protein prescribed (Table 8). During this period, the control subjects received a daily average of 1121±50 mmol of nitrogen/day (15.7±0.7 g/day) and excreted 1414±107 mmol/day (19.8±1.5 g/day) which resulted in a negative nitrogen balance of −300±86 mmol/day (−4.2±1.2 g/day). The glutamine-supplemented patients received 1164±57 mmol nitrogen/day (16.3±0.8 g/day) and excreted 1271±71 mmol/day (17.8±1.0 g/day) which accounted for a nitrogen balance of −100±36 mmol/day (−1.4±0.5 g/day). This nitrogen loss was significantly less than that of the patients receiving standard solutions ($p < 0.002$, Table 8). When nitrogen balance was assessed in the statistical model using analysis of variance, balance was unrelated to sex or weight of the patient, nitrogen intake, average daily or maximum daily temperature, C-reactive protein concentration or antibiotic use. Treatment (± glutamine) accounted for the greatest portion of the variability in this model and was significant at the $p < 0.01$ level. Interpatient variability and post transplant day were the other factors which were significant at the $p < 0.01$ and $p < 0.04$ levels, respectively. The glutamine effect on nitrogen balance remained statistically significant even when the model was adjusted for the variation contributed by these other covariables.

TABLE 8
Nutrient Intake And Balance Data
Means ± S.E.M.

| Entire TPN Course | Standard | Glutamine-supplemented |
|---|---|---|
| N | 11 | 13 |
| Duration of TPN (days) | 28 ± 1 | 28 ± 3 |
| IV Calories (kcal/day) | 2360 ± 77 | 2310 ± 83 |
| IV nitrogen (g/day) | 13.7 ± 0.5 | 14.6 ± 0.7 |
| Oral calories (kcal/day) | 305 ± 34 | 276 ± 48 |
| Oral nitrogen (g/day) | 1.1 ± 0.3 | 0.98 ± 0.2 |
| Initial 7 day Balance Period |  |  |
| N | 11 | 12 |
| IV calories (kcal/day) | 2553 ± 76 | 2470 ± 98 |
| IV nitrogen (g/day) | 14.9 ± 0.6 | 15.9 ± 0.7 |
| Oral calories (kcal/day) | 153 ± 19 | 185 ± 41 |
| Oral nitrogen (g/day) | 0.4 ± 0.2 | 0.3 ± 0.2 |
| Nitrogen balance (g/day) | −4.2 ± 1.2 | −1.4 ± 0.5* |
| Cumulative nitrogen balance (g/7 days) | −29.6 ± 8.6 | −9.7 ± 3.4* |
| Creatinine excretion (mmol/d) | 12.6 ± 0.9 | 11.0 ± 0.9 |
| (g/day) | (1.43 ± 0.10) | (1.24 ± 0.10) |
| 3-methylhistidine excretion (μmol/day) | 168.1 ± 15.2 | 121.4 ± 12.1+ |
| 3-methylhistidine/creatinine ratio (mol/mol × $10^{-3}$) | 13.3 ± 0.9 | 10.9 ± 0.4+ |
| Average daily temperature (°C.) | 37.6 ± 0.2 | 37.4 ± 0.2 |
| Average daily peak temperature (°C.) | 38.2 ± 0.2 | 38.0 ± 0.2 |
| C-reactive protein (mg/L) | 62.7 ± 13.4 | 45.5 ± 10.3 |
| Patients receiving antibiotics (on/off) | 8/3 | 7/5 |

*$p < 0.002$ by Mann-Whitney Test;
+$p = 0.03$ by Student's t-test
To convert nitrogen to mmol, multiply by 71.4
To convert kcals to kjoules, multiply by 4.184

Creatinine excretion was comparable in the two groups but the 3-methylhistidine/creatinine ratios were significantly difference during the initial study period, suggesting a decrease in myofibrillar protein breakdown in the patients receiving glutamine (Table 8).

There was no evidence to indicate that the difference in nitrogen balance between the two groups during the initial balance period was related to differences in the severity of illness. For example, mean weekly temperature, mean daily peak temperature and average concentration of C-reactive protein, all markers of acute inflammation and/or infection, were comparable during and before this study period (Table 8). Moreover, a comparable proportion of patients from each group was receiving antibiotics at the time of study.

What is claimed is:

1. A method of decreasing tissue breakdown in a mammal, comprising administering to said mammal a therapeutically effective amount of a composition wherein said composition comprises from about 35% to 50% essential amino acids, from about 50% to 65% non-essential amino acids, and from about 18% to 30% branched chain amino acid; wherein said non-essential amino acids comprise from about 10% to 25% ALA and from about 15% to 45% GLN.

2. The method of claim 1, wherein said mammal is a human.

3. The method of claim 1, wherein said composition is administered parenterally.

4. The method of claim 1, wherein said composition is administered enterally.

5. The method of any one of claims 1-4, wherein said composition additionally contains from about 10-25% glucose.

6. The method of claim 1, wherein said tissue breakdown results from an acute catabolic state.

7. The method of claim 6, wherein said acute catabolic state is selected from the group consisting of burns, trauma, infection, radiation and chemotherapy.

8. The method of claim 1 wherein said tissue breakdown results from the administration of an anti-inflammatory agent.

9. A composition comprising from about 35% to 50% essential amino acids of which from about 18% to 30% are branched chain amino acids, and from about 50% to 65% non-essential amino acids; wherein said non-essential amino acids comprises from about 5% to 15% ALA and from about 15% to 45% GLN.

10. The composition of claim 9 further comprising from about 10-15% glucose.

* * * * *